United States Patent [19]

Lang

[11] 4,093,516

[45] June 6, 1978

[54] PREPARATION OF LIQUID FUEL AND NUTRIENTS FROM MUNICIPAL WASTE WATER

[76] Inventor: John L. Lang, P.O. Box 1242, Midland, Mich. 48640

[21] Appl. No.: 509,813

[22] Filed: Sep. 27, 1974

[51] Int. Cl.$^2$ .............................................. C12B 1/00
[52] U.S. Cl. ........................................ 195/27; 127/36; 195/32; 210/2; 426/7; 426/53
[58] Field of Search ................... 195/28 R, 32, 33, 34, 195/82, 91, 31 P, 27; 210/7, 8, 2, 15, 4, 18, 40, 59; 127/36; 426/7, 53

[56] References Cited

U.S. PATENT DOCUMENTS

| | | | |
|---|---|---|---|
| 2,123,211 | 7/1938 | Scholler | 195/33 |
| 3,676,334 | 7/1972 | Zukerman et al. | 210/18 X |
| 3,711,392 | 1/1973 | Metger | 195/33 X |
| 3,772,188 | 11/1973 | Edwards | 210/63 |

*Primary Examiner*—R. B. Penland

[57] ABSTRACT

The organic portion of the impurities in municipal waste are converted into a liquid fuel suitable for use in internal- and external-combustion engines, a residue suitable for animal feed supplement and purified water by the process which comprises the steps of: partial concentration, saccharification, fermentation and distillation.

9 Claims, 1 Drawing Figure

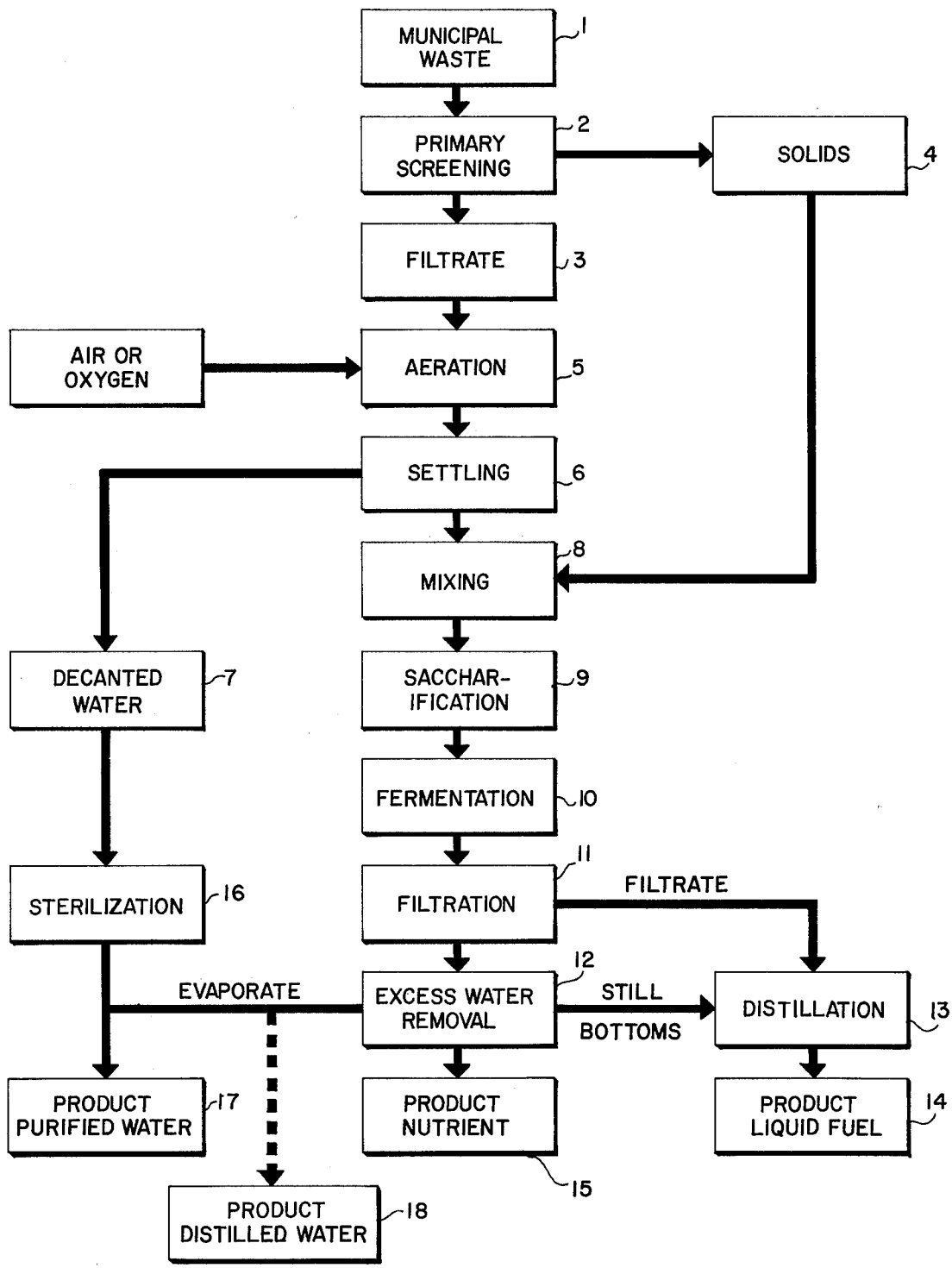

PREPARATION OF LIQUID FUEL AND NUTRIENTS FROM MUNICIPAL WASTE WATER

BACKGROUND OF THE INVENTION

The problem involved in treatment for disposal of municipal waste concerns the "ultimate disposal" of the noxious material therein.

The ultimate disposal of liquidous wastes, especially municipal waste or (sewage) is a perplexing, expensive problem.

The present partial solutions to the problem include the primary treatment of such wastes, which involve merely the removal of the gross contaminants; secondary treatment involving a partial digestion of the contaminating solids, using air or even oxygen sparging to both promote the metabolic process of aerobic microbes while suppressing the growth and/or reproduction of anaerobic species, such as the clostridii, which produce very toxic metabolic by-products. Present methods may involve expensive filtration steps, and sometimes sterilization, and these processes constitute the total of the treatment given municipal waste by the vast majority of municipal waste-treatment plants in existence, or even contemplated. The product of such plants may consist of 96–99.5% water, but it is a gray suspension, susceptible to conversion to septic material in about 20 minutes, and is not only non-palatable but repugnant in appearance and odor.

These conventional processes merely, for the most part, convert one form of nuisance into another form, and the problem of "ultimate disposal" in some harmless, or preferably useful, form largely remains unsolved.

The conventional processes of disposal of municipal waste, i.e., sewage, treatment, specifically those other than mere burial, usually involve the oxidation of the organic constituents therein, whether by incineration or wet-oxidation methods, both direct and biological, are a fearful waste both of the compounds therein and of the fuel required in all cases. The organic constituents were formed by consumption of the energy required for their synthesis, by either sunlight or man's expenditure of energy thereupon; e.g., that energy used in the manufacture of synthetic fertilizers, and the waste incurred by merely burning them to get rid of them is obvious. Also, the fuel-fired drying and incineration consumes fuels in such a way that no useful purpose is served in terms of recovery of such energy requirements and the energy stored in the components being destroyed.

This wastage is best illustrated by the fate of the nitrogenous compounds in municipal waste. These compounds are the main source of nuisance in such wastes, but the synthesis thereof required extensive amounts of energy, particularly when they were derived from synthetic fertilizers. The incineration of such compounds converts them almost exclusively to free nitrogen gas; the re-fixation of the nitrogen gas for conversion to nitrogen-containing fertilizers requires a further expenditure of energy. This re-fixed nitrogen absurdly enough is often synthesized to the same kinds of nitrogenous compounds which are originally present in the municipal waste; thus certain of the conventional procedures constitute a cycle, but the net result is the waste of the energy required for continual re-formation of nitrogenous compounds from free atmospheric nitrogen.

It is true that certain conventional municipal waste disposal processes produce nitrogenous fertilizer; however, these materials are ordinarily non-sterile. It is a historical fact that civilizations using natural animal waste fertilizers, especially those which use human waste, have endemic dysentery as a continual problem.

The use of fossil fuels for production of various forms of energy to continually destroy and reform such nitrogenous compounds drains exhaustible energy sources.

It would be extremely desirable to use compounds produced every day by the sun as a source of fuels, and especially liquid (fluid) fuels, which are more easily transported and stored than other fuel forms.

Thus, there remain the several problems of practical concentration, sterility, and ultimate disposal of municipal waste, plus the desirability of recovery of the energy represented by the composition thereof.

In the process of this invention the solid organic portion of the impurities of Municipal waste water is concentrated, saccharified to a fermentable state by heatings, then fermented, and the combustible fraction therein separated, e.g. by distillation; thus producing liquid fuel such as that useable in production of energy, and also residue suitable for animal feed, and purified water.

SUMMARY OF THE INVENTION

This invention concerns an ultimate disposal method for municipal waste, i.e. sewage, to produce useful products. Heretofore, said municipal waste has not been converted to these useful products, but discarded in much less useful forms, and in most cases, it has been discarded as a nuisance.

This process comprises the combined steps of separation, either simultaneously or consecutively with a chosen concentration step, of the solid components of said municipal waste, followed by microbial conversion of the soluble contaminants therein, which enables the separation of, and innocous disposal of the major volume of said waste, followed by conversion of said separated solid components of said waste to a fermentable mixture, fermentation of said fermentable mixture, and separation of the end products of the fermentation to produce a valuable nutrient fraction and a valuable fuel fraction, usable, e.g. as fuel for an internal combustion engine, as a source of other forms of energy such as electrical power or heat.

Thus the object of this invention is to both provide a means for the ultimate disposal of municipal waste and simultaneously produce therefrom liquid fuel, high nitrogenous-content nutrients, and purified water.

Another object of this invention is to provide for the ultimate disposal of municipal waste in a useful form, in contrast with the concentrated, but still obnoxious materials produced by some conventional methods.

A further object of this invention is to provide a liquidous fuel, suitable for use in heating, and electric power generation.

Another object of this invention is to provide a liquidous fuel suitable for use in an internal combustion engine.

MORE PARTICULAR DESCRIPTION OF THE INVENTION

The steps of the process for accomplishing the above objects are comprised essentially of those outline in FIG. 1. The municipal waste water 1 is put through a primary screening step 2, being separated into Filtrate 3 and gross or large size solids 4. The Filtrate 3 is then aerated by air or oxygen sparging or otherwise contacting therewith in Aeration step 5. The effluent from Aeration 5 is then passed to a Settling step 6, with or without addition of suitable settling agents, and the clear supernatant water separated into Decanted water 7 and the settled solids passed to mixing step 8, where it is recombined with the gross Solids 4 obtained from the Primary Screening step 2, and mixed until more or less uniform in flow character. The non-aqueous contaminants are then converted, at least partially, to sugars in the Saccharification step 9. It will be realized that the mixing step 8 and the Saccharification step 9 can be carried out in the same vessel, or separately, as desired. The Saccharification step 9 can be carried out with suitable application of heat in the presence of air as oxygen, or in the presence of suitable hydrolytic agents as air, oxygen, $SO_2$, or other acidic media, etc. After proper saccharification, the pH of the molasses-like material is adjusted, and the composition adjusted suitably for fermentation by, e.g. Saccharomyces cervasii, which is carried out in Fermentation step 10. When a suitable degree of conversion of the fermentable sugars is obtained, the product of Fermentation step 10 is filtered in Filtration step 11, the residue passed to Excess Water Removal step 12. The filtrate from the step 11 is charged to the Distillation unit of step 13, and the overhead liquid fuel product 14, collected for use. The residue from the Distillation step 13 is sent to the Excess Water Removal unit 12, here it and the residue from Filltration step 11 are de-watered to a consistency suitable for use as animal and plant nutrients; partial dewatering giving a syrupy product suitable for use as a binder for other materials as grains, peat moss, etc., and the resulting mixture flaked, pelletized, or otherwise prepared for nutrient use as the Product Nutrient 15, or de-watered to a concentration suitable for use per se as Product Nutrient 15.

The water removed in the Excess Water Removal step 12 may be used per se, if desired, as a distilled water 18, or combined with water from step 6 after sterilization in Sterilization step 16, giving Product Water 17.

Suitable aids for the hydrolysis and saccharification step include molecular or nascent oxygen, ozone, proton-rich materials as mineral and organic acids, especially those having sulfur or phosphorous as the central atom of the anionic portion of the molecule, and combinations thereof.

The hydrolysis and saccharification are hastened by proper adjustment of temperature, type and amount of the hydrolytic agent, and the concommitant pressure required for maintainance of the temperature selected for use in the hydrolysis and saccharification step.

The following Examples are given merely to illustrate the invention, and are not to be construed as limiting the claims in any way;

EXAMPLE I

Municipal waste sludge was introduced into a corrosion-resistant pressure vessel, and the pressure increased by means of heat and air sparged therethrough, at a temperature of 200° C and a pressure of about 350 pounds per square inch (guage) to saccharify the organic materials in the sludge, during which process the organic materials are solubilized to a greater degree and the remaining insolubles are mainly inorganic in character. At this stage, the saccharified product contains about 8–10% total solids, of which about 5–7% is organic material, and the pH is about 6.

The saccharified material was cooled and concentrated by passing through a falling-film evaporator, operated so that the effluent temperature was 65° C and the organic solids content was about 30%. The pH was adjusted to a value of 3.4, and a small amount of enzymes, e.g., in the form of barley malt, was added. This enzyme-containing mixture was maintained at 65° C for 3 hours.

After cooling to 27° C and re-adjustment of the pH to a value of 3.4, yeast was added and the temperature and pH maintained until fermentation ceased. The fermented material was filtered, the residuum steam sterilized and stored. The filtrate was distilled, using a four-foot column packed with porcelain chips, fitted with a take-off head which was regulated at a reflux-ratio of 20:1. The still-pot heating was regulated to maintain a temperature in the vicinity of 76°–80° C.

Based upon an initial charge of 100 parts to the still-pot, the distillate was 11.5 parts of ethanol-water mixture. The ethanol was, optionally, dried with calcium oxide, filtered and this product mixed 1:9 with gasoline. This liquid fuel mixture, after minor carburator adjustment, was found to burn cleanly and well in a conventional internal combustion engine.

The filtered residuum from the fermentation step was re-combined with the still-pot residuum, and the whole evaporated until a thick syrup was formed, distilled water being formed as a by-product. This syrup was combined with ground feed grains, the syrup acting as both a binder for pelleting same, as well as containing the sterilized, cooked nutritive values of the municipal waste and the nutritive values of the yeasts in the fermentation residuum, which yeasts multiplied, of course, during the fermentation step.

EXAMPLE II

Eight gallons of partially de-watered, activated sludge, having a total solids of 8% was placed in a corrosion-resistant pressure vessel fitted with an agitator, electrical heating element and thermocouple well. The pH of the sludge was lowered to a value of 1.5 by the addition of sulfurous acid ions. After sealing the reactor and beginning agitation, the electrical heating system was adjusted to maintain a temperature of 140° C, and heating and agitation continued for 3.5 hours.

The contents of the reactor were then discharged into an expansion chamber, and sparged with steam and the pH was adjusted to 3.4. After cooling to 65° C, enzymes in the form of barley malt, were added and these condions of temperature and pH maintained for 4 hours. The temperature was lowered to 27° C, and the pH adjusted to 3.4. Yeast was added and fermentation begun. These fermentation conditions were maintained until the fermentation ceased.

The fermented material was filtered, and the residuum steam sterilized and stored for use later. Distillation, per 100 parts of the filtrate gave 3.4 parts of ethanol-water azeotrope containing 95% ethanol. Mixture of this product at a ratio of 1:9 with ordinary gasoline burned well and cleanly in a conventional internal combustion engine, after minor adjustment of the carburetor.

Thus a city discharging daily 1 million gallons of such municipal waste, by suitable conversion, would produce about 34,500 gallons of liquid motor fuel plus approximately 80 tons of highly nutritious animal feed supplement per day.

I claim:

1. The process for preparation of useful substances, including liquid fuel stock and nutrient materials from liquidous municipal waste which comprises essentially the steps of:
   (a) adjustment of the solids content of said liquidous waste;
   (b) hydrolysis and saccharification of the polysaccharides and other components of said liquidous waste in the presence of an essentially constant concentration of a hydrolytic agent selected from the group consisting of oxygen, ozone, and acidic compounds of sulfur and phosphorus, and carried out to the extent that the organic portion of the liquidous waste is essentially solubilized and sterilized;
   (c) rendering innocuous the hydrolytic agent of step (b);
   (d) adjustment of the soluble solids content and the pH of the so-obtained mixture to provide a suitable environment for fermentation of said mixture;
   (e) innoculation of said sterile mixture with a selected essentially single fermentation species, and, when desired, with enzymatic materials;
   (f) fermentation of said mixture under conditions suitable for metabolic action by said fermentation species; and
   (g) isolation of the desired product components from the fermented mixture.

2. The process of claim 1, wherein the liquidous municipal waste is sewage.

3. The process of claim 1, wherein the hydrolysis is brought about by oxygen.

4. The process of claim 1, wherein the hydrolysis is brought about by ozone.

5. The process of claim 1, wherein the hydrolysis and saccharification is catalyzed by the reaction product of sulfur dioxide with the components of the liquidous waste.

6. The process of claim 1, wherein the hydrolysis, saccharification, and sterilization is brought about by a compound formed from sulfur dioxide.

7. The process of claim 1, wherein the hydrolysis and saccharification is catalyzed by a compound which has a sulfur atom as a central atom of the anion thereof.

8. The process of claim 1, wherein the hydrolysis and saccharification is catalyzed by a compound which has a phosphorus atom as the central atom of the anion thereof.

9. The process of claim 1, wherein the liquid fuel product is ethanol.

* * * * *